(12) United States Patent
Okada

(10) Patent No.: US 10,182,835 B2
(45) Date of Patent: Jan. 22, 2019

(54) STONE EXTRACTION AND FRAGMENTATION DEVICE

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/349,039

(22) Filed: Nov. 11, 2016

(65) Prior Publication Data

US 2017/0056033 A1    Mar. 2, 2017

Related U.S. Application Data

(63) Continuation of application No. PCT/JP2015/079583, filed on Oct. 20, 2015.

(30) Foreign Application Priority Data

Oct. 24, 2014   (JP) ................................. 2014-217193

(51) Int. Cl.
   *A61B 17/221*     (2006.01)
   *A61B 17/29*      (2006.01)
   *A61B 17/00*      (2006.01)

(52) U.S. Cl.
   CPC .... *A61B 17/221* (2013.01); *A61B 2017/0046* (2013.01); *A61B 2017/00477* (2013.01); *A61B 2017/2212* (2013.01); *A61B 2017/2217* (2013.01); *A61B 2017/2923* (2013.01)

(58) Field of Classification Search
   CPC ..................... A61B 17/221; A61B 2017/2217
   See application file for complete search history.

(56) References Cited

U.S. PATENT DOCUMENTS 4,741,335 A    5/1988  Okada
4,768,505 A    9/1988  Okada et al.
(Continued)

FOREIGN PATENT DOCUMENTS

DE   10 2010 007194 A1    8/2011
JP        S62-258650 A    11/1987
(Continued)

OTHER PUBLICATIONS

International Search Report dated Jan. 12, 2016 issued in PCT/JP079583.
(Continued)

*Primary Examiner* — Kathleen Holwerda
*Assistant Examiner* — Christina Lauer
(74) *Attorney, Agent, or Firm* — Scully, Scott, Murphy & Presser, P.C.

(57) ABSTRACT

A stone extraction fragmentation device of the present invention include: a stone extraction operation section having a first main body and a gripping section; and a fragmentation operation section having a second main body, a moving body which is capable of being connected with the first main body, and a rotating knob which is configured to move the moving body with respect to the second main body, wherein the moving body is configured to move the first main body in a direction away from the second main body by rotation of the rotating knob.

16 Claims, 18 Drawing Sheets

(56) References Cited

U.S. PATENT DOCUMENTS

| | | | |
|---|---|---|---|
| 6,419,679 B1* | 7/2002 | Dhindsa | A61B 17/221 606/113 |
| 2002/0026202 A1 | 2/2002 | Honey et al. | |
| 2011/0184345 A1 | 7/2011 | Howell et al. | |
| 2014/0121458 A1* | 5/2014 | St. George | A61B 1/00066 600/107 |

FOREIGN PATENT DOCUMENTS

| | | |
|---|---|---|
| JP | H1-80111 U | 5/1989 |
| JP | H5-116 U | 1/1993 |
| JP | 2006-314714 A | 11/2006 |
| JP | 2006-314715 A | 11/2006 |
| JP | 2009-541006 A | 11/2009 |
| WO | WO 2008/002417 A2 | 1/2008 |

OTHER PUBLICATIONS

Extended Supplementary European Search Report dated May 28, 2018 in European Patent Application No. 15 85 2913.1.
Chinese Office Action dated Jun. 5, 2018 in Chinese Patent Application No. 201580024890.2.

* cited by examiner

STONE EXTRACTION AND FRAGMENTATION DEVICE

This application is a continuation application, based on PCT/JP2015/079583, filed on Oct. 20, 2015, claiming priority based on Japanese Patent Application No. 2014-217193, filed in Japan on Oct. 24, 2014, the content of which is incorporated herein by reference.

FIELD OF THE INVENTION

The present invention relates to a stone extraction and fragmentation device.

DESCRIPTION OF THE RELATED ART

A procedure in which a stone is fragmented and removed and a procedure in which stone is extracted without being fragmented and is removed are known as a procedure in which a stone, which appears inside an organ such as a bile duct or a urinary bladder, is removed.

When a stone is to be fragmented, it is known that the treatment is endoscopically performed using a stone fragmentation device which is configured to be inserted into an endoscope. In a general procedure to fragment a stone, the stone is captured in a basket section which projects from a distal end of an insertion section. After that, a portion of the basket section is retreated to the insertion section, the stone is clamped, and the stone is fragmented (for example, refer to Japanese Unexamined Patent Application, First Publication No. 2006-314715).

Generally, when it is diagnosed that the stone has size in which the stone does not need to be fragmented, a stone extraction device which includes a basket section configured to extract a stone and an operation section configured to expand and contract the basket section is used. The stone extraction device has a simple operation section in many cases since it is not expected to apply a force which is necessary to crush the stone.

On the other hand, a stone fragmentation device has an operation section having a complicated structure in many cases so as to efficiently transfer a force, which is necessary to fragment a stone, to a basket.

If a stone extraction device is used to remove a stone without fragmenting the stone, in case when it becomes necessary to fragment the stone in a body, the stone extraction device should be replaced by a stone fragmentation device.

SUMMARY OF THE INVENTION

Means for Solving the Problem

An aspect of the present invention is a stone extraction and fragmentation device including: a cylindrical insertion section which is capable of being inserted into a channel of an endoscope; a treatment section which is located at a distal end of the insertion section; an operation wire which is inserted in the insertion section to be able to be advanced or retreated and drives the treatment section; a first main body which is connected to the proximal end of the insertion section; a gripping section to which the operation wire is connected and which is capable of being advanced or retreated with respect to the first main body; a second main body which is capable of being connected to the gripping section; a moving body which is disposed at the second main body and capable of being connected to the first main body; and a rotating knob which is disposed at the second main body and configured to cause the moving body to be advanced or retreated with respect to the second main body, wherein the moving body is configured to move the first main body in a direction away from the second main body by rotation of the rotating knob.

The operation wire and the moving body may be configured to be advanced and retreated along different axes from each other.

The stone extraction and fragmentation device according to the above aspect may include, a first operation section which is provided at a proximal end of the insertion section; and a second operation section which is capable of being attached to and detached from the first operation section, wherein the first operation section has the first main body and the gripping body, and the second operation section has the second main body, the moving body, and the rotating knob.

The second operation section may be configured to operate the gripping section moving in a direction away from the first main body in accordance with moving the moving body in a direction away from the second operation section using rotation of the rotating knob.

DETAILED DESCRIPTION OF THE INVENTION

First Embodiment

Figure 1:
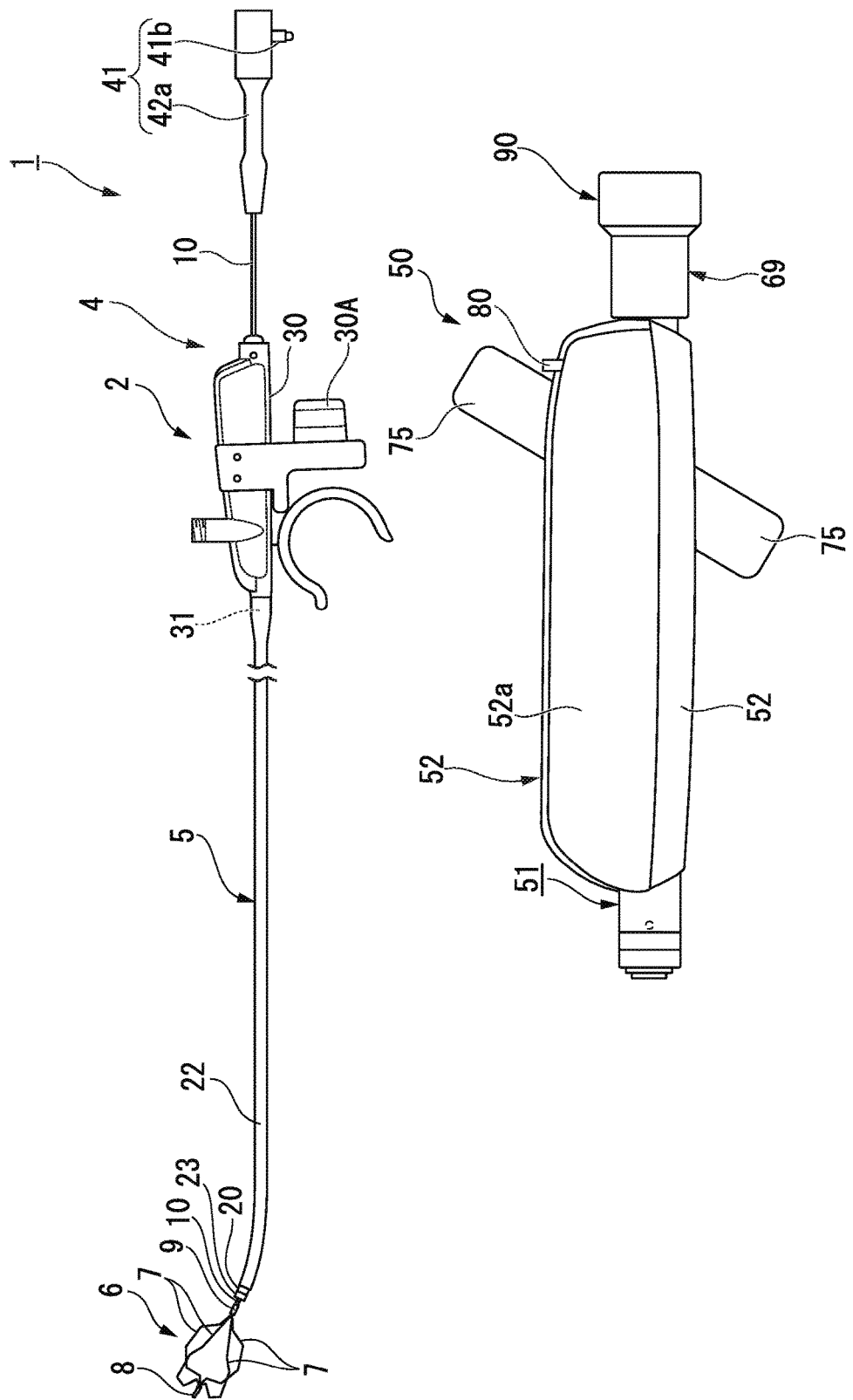
FIG. 1 is an overall diagram showing a stone extraction and fragmentation device of a first embodiment of the present invention.
Figure 2:
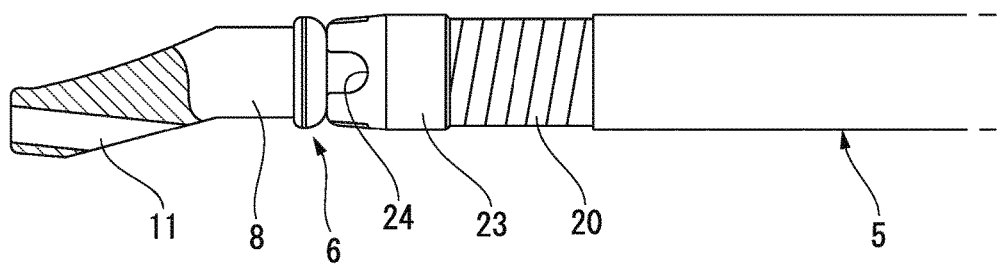
FIG. 2 is a side view showing a portion of a fragmenting tool of the stone extraction and fragmentation device.
Figure 3:
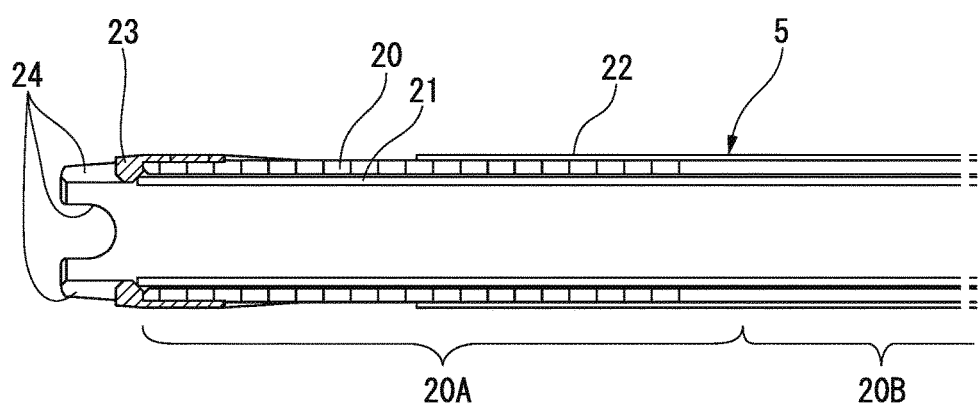
FIG. 3 is a cross-sectional view showing a portion of the fragmenting tool of the stone extraction and fragmentation device.
Figure 4:
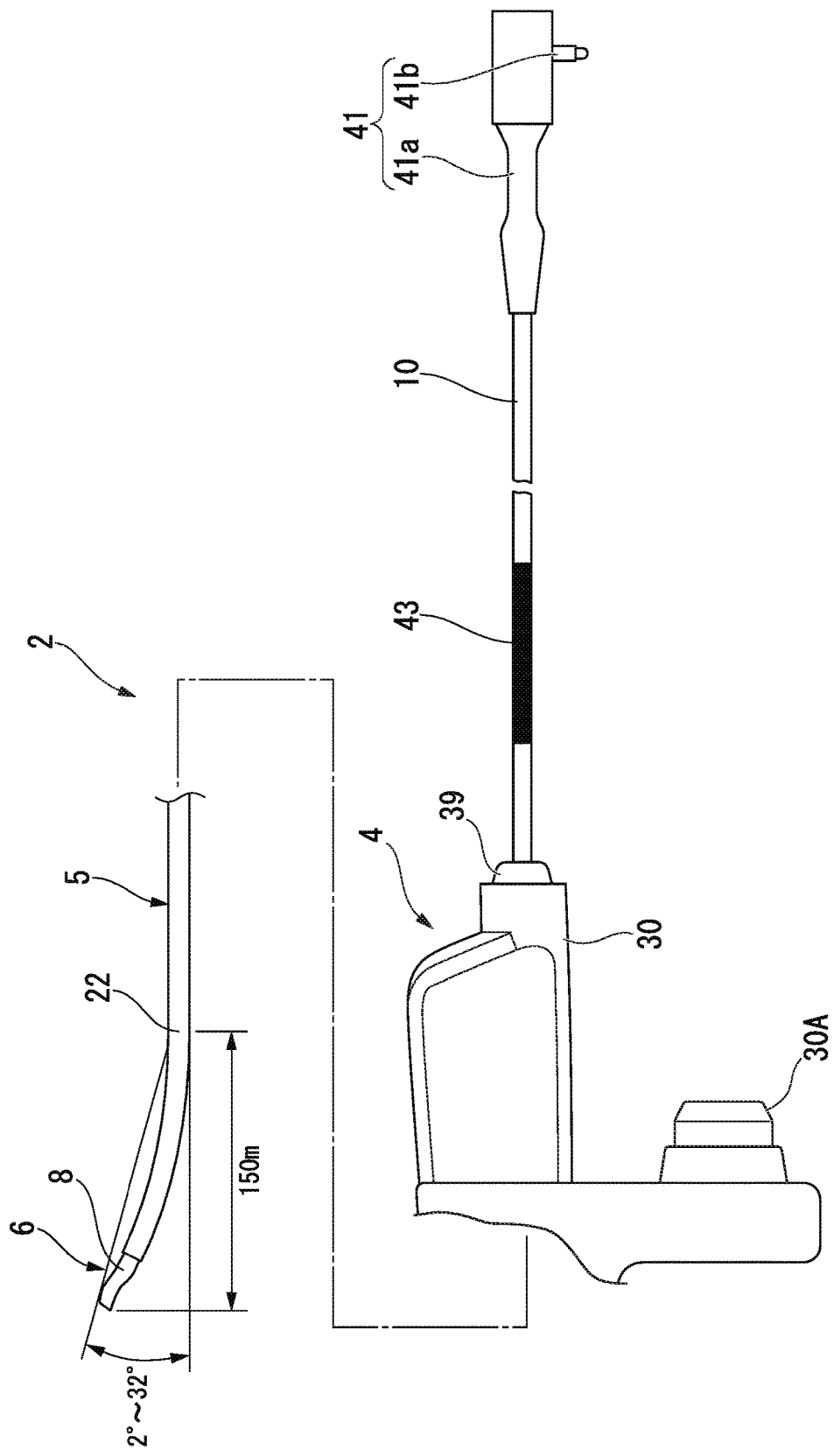
FIG. 4 is an enlarged view showing the fragmenting tool of the stone extraction and fragmentation device.
Figure 5:
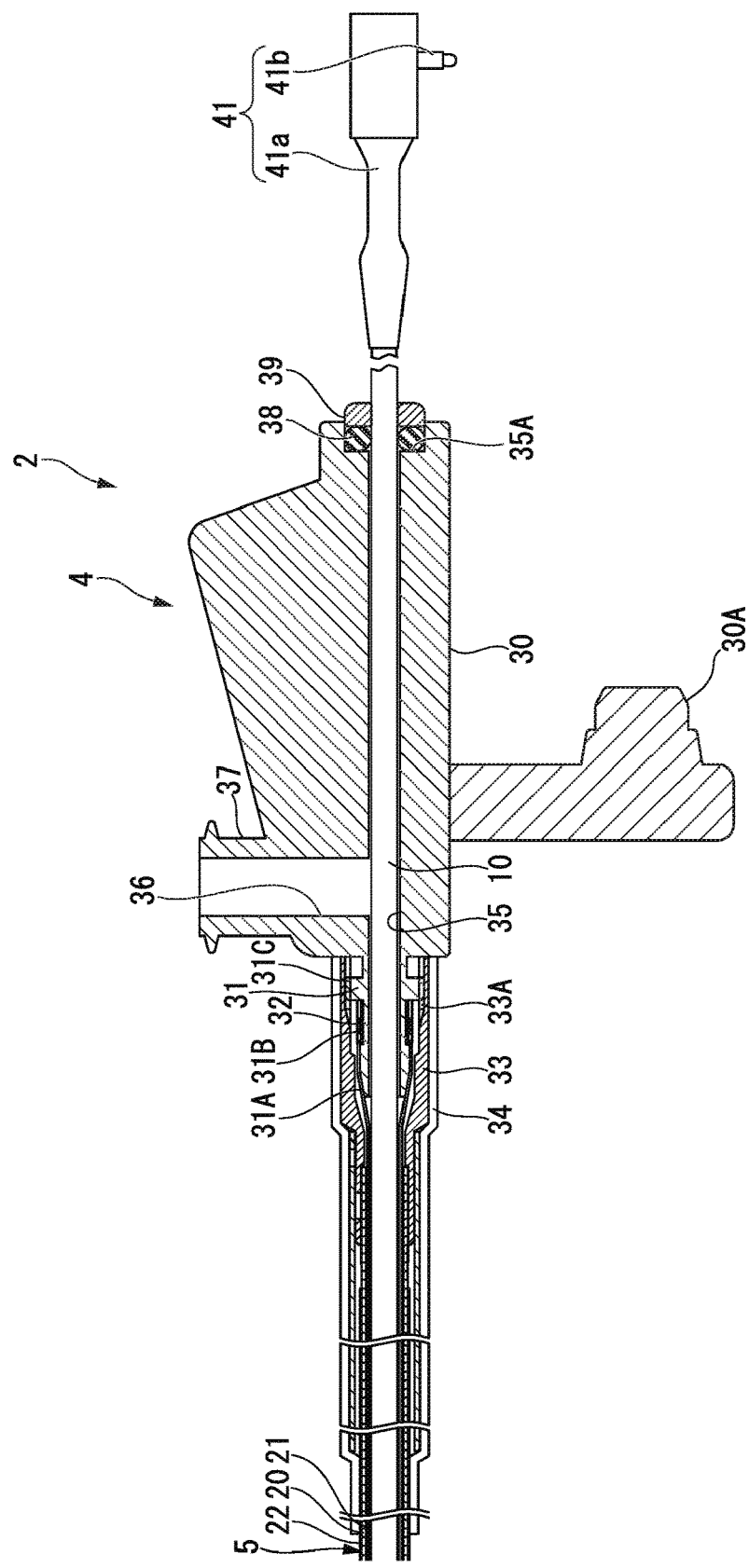
FIG. 5 is a cross-sectional view showing a stone extraction operation section of the stone extraction and fragmentation device.

Hereinafter, an embodiment of the present invention will be described in detail with reference to the drawings. FIG. 1 is an overall diagram showing a stone extraction and fragmentation device 1 of this embodiment. FIG. 2 is a side view showing a portion of a fragmenting tool 2 of the stone extraction and fragmentation device 1. FIG. 3 is a cross-sectional view showing a portion of the fragmenting tool 2 of the stone extraction and fragmentation device 1. FIG. 4 is an enlarged view showing the fragmenting tool 2 of the stone extraction and fragmentation device 1. FIG. 5 is a cross-sectional view showing a stone extraction operation section 4 of the stone extraction and fragmentation device 1.

The stone extraction and fragmentation device 1 of this embodiment shown in FIG. 1 is configured to be used with being inserted in an endoscope and is used for a procedure in which a stone in a body is extracted or fragmented.

As shown in FIG. 1, the stone extraction and fragmentation device 1 has the fragmenting tool 2 and a stone fragmentation operation section 50 (a second operation section) which can be attached or detached with respect to a stone extraction operation section (a first operation section) 4 of the fragmenting tool 2.

The fragmenting tool 2 has the stone extraction operation section 4, an elongated insertion section 5 which extends from a distal end of the stone extraction operation section 4, and a basket section 6 configured to be a treatment section which is capable of being driven as freely protrudes from and retracts into a distal end of the insertion section 5.

The basket section 6 has a plurality of elastic wires 7. Distal end sections of the elastic wires 7 are bound as a single body by a distal end tip 8. Proximal ends of the elastic wires 7 are fixed to a distal end section of an operation wire 10 in a state of being bound by a joint member 9. The elastic wires 7 have a plurality of bent sections between the distal end tip 8 and the joint member 9. The elastic wires 7 are constituted to expand in a cage shape in their natural state. Here, a portion of the basket section 6 other than the distal end tip 8 can be housed inside the insertion section 5. The distal end tip 8 of the basket section 6 is made of an elastic member. As shown in FIG. 2, a hole 11 passes through the distal end tip 8 to a lateral section from a distal end of the distal end tip 8. Also, the distal end tip 8 is bent to be offset with respect to a portion near an opening of a lateral section side of the hole 11 and is formed in a substantial S shape as a whole.

As shown in FIGS. 2 and 3, the insertion section 5 is a flexible cylindrical member. The insertion section 5 has a coil sheath 20, a tubular sheath 21 which is disposed inside the coil sheath 20, and an outer sheath 22 which covers an outer circumference of the coil sheath 20. The operation wire 10 is inserted into the tubular sheath 21 to be freely advanced or retreated.

The coil sheath 20 is manufactured by closely winding a metallic flat plate. In the coil sheath 20, a soft section 20A with relatively high flexibility is formed at a distal region of the sheath 20 by modifying a degree of closeness between adjacent flat plates. A portion of the coil sheath 20 that is closer to a proximal end side than the soft section 20A is a hard section 20B with lower flexibility than that of the soft section 20A. An example of a technical method of forming the soft section 20A includes modifying tension when winding the coil sheath 20. Note that the method of forming the soft section 20A is not limited thereto.

A distal end cover 23 is fixed to a distal end section of the coil sheath 20 using brazing, laser welding, etc. The distal end cover 23 is made of an annular metal. Concave sections 24 which can receive the elastic wires 7 are formed in a distal end section of the distal end cover 23 to correspond to the number of the elastic wires 7.

When a stone is fragmented, the elastic wires 7 enter the concave sections 24 so that a clamping force at the stone fragmentation operation section 50 acts on the stone via the insertion section 5.

The tubular sheath 21 is made of a resinous tube. The tubular sheath 21 makes the basket section 6 and the operation wire 10 easily rotatable around an axis as a result from which the tubular sheath 21 is inserted between the metallic coil sheath 20 and the metallic operation wire 10. Also, the tubular sheath 21 makes the basket section 6 easily be expanded and compressed as a result from which the tubular sheath 21 is inserted between the metallic coil sheath 20 and the metallic operation wire 10.

The outer sheath 22 is manufactured by, for example, a fluorine-based resin. In this embodiment, the outer sheath 22 has a bending tendency (a pre-curve) in which a distal end section of the insertion section 5 is bent in its natural state. The insertion section 5 is bent with respect to the axis due to the bending tendency of the outer sheath 22. For example, in a state that the basket section 6 is housed in the insertion section 5, the insertion section 5 is moderately in bent shape due to the bending tendency of the outer sheath 22 within a range of 2° to 32° with respect to the axis which is closer to the proximal end than a origination which is at 150 mm distant from the distal end of the distal end tip 8.

As shown in FIG. 5, the stone extraction operation section 4 has a first main body 30, a fixing section 31 which integrally protrudes from a distal end side of the first main body 30, and a gripping section 41 which is fixed to a proximal end of the operation wire 10 to be described below.

The first main body 30 is formed with an insertion hole 35 which passes through the first main body 30 in an axial direction to a proximal end of the first main body 30 from a distal end of the fixing section 31 and with a communication hole 36 which branches from the insertion hole 35 in the middle of the insertion hole 35. Also, an substantially cylindrical-shaped engagement protrusion 30A which is engaged with a joint 90 of the stone fragmentation operation section 50 to be described below is formed on the first main body 30.

The insertion hole 35 is a through hole through which the operation wire 10 is inserted to be freely advanced or retreated.

The communication hole 36 is opened to an outer circumferential section of the first main body 30. A peripheral section of the communication hole 36 is formed with a ferrule 37 which can connect a syringe or the like.

When a syringe in which a contrast agent or the like is filled is connected with the ferrule 37, the contrast agent or the like can be injected into the body via the ferrule 37. In addition, a portion of the insertion hole 35 that is closer to the proximal end side than a position at which the communication hole 36 is formed is enlarged in diameter, and a sealing member 38 such as an O ring is inserted into an enlarged diameter portion 35A.

The sealing member 38 provides a liquid-tight structure between the first main body 30 and the operation wire 10 which is inserted to be freely advanced or retracted in the insertion hole 35. A cap 39 is screwed on a portion which is closer to the proximal end side than the sealing member 38.

The cap 39 has a through hole through which the operation wire 10 is inserted.

The fixing section 31 has a substantially tubular shape. An outer circumference of the fixing section 31 is sequentially formed with a tapered surface 31A, a diameter of which is reduced toward a distal end thereof, a concave section 31B which catches the tubular sheath 21, and a male screw 31C from the distal end side. The outer circumference of the fixing section 31 is inserted into the proximal end of the tubular sheath 21. The tubular sheath 21 is fixed by winding a thread 32 around a portion corresponding to the concave section 31B. In addition, a cover member 33 in which a female screw 33A is carved is threadedly engaged with the male screw 31C. The cover member 33 is made of a metallic material. A proximal end of the coil sheath 20 is brazed at an inner circumferential side of a distal end section of the cover member 33. An outer cylindrical member 34 is press-fitted to the cover member 33 to cover an outer circumferential surface thereof.

The operation wire 10 extends to pass through the stone extraction operation section 4. The gripping section 41 is fixed to the proximal end of the operation wire 10. As shown in FIG. 4, a marking 43 is provided at the operation wire 10. The marking 43 is formed at a position at which the marking 43 is exposed to the outside from the stone extraction operation section 4 when the operation wire 10 is pulled from the stone extraction operation section 4 and the basket section 6 is driven to be housed inside the insertion section 5.

The gripping section 41 is a member which is fixed to the operation wire 10 such that an operator can grip the gripping section 41 to move the operation wire 10.

The gripping section 41 has a rod-shaped section 41a which is formed in a rod shape which is thicker than that of the operation wire 10, and a pin 41b by which the gripping section 41 is joined to a cover 52b of the stone fragmentation operation section 50 which will be described below.

A circumference of the pin 41b in an outer surface of the gripping section 41 has a shape which follows an outer surface shape of the cover 52b. Also, a surface which is opposite to the pin 41b in the outer surface of the gripping section 41 has a flat or gentle curved shape such that the operator easily presses and fixes the gripping section 41 with respect to the cover 52b. The outer surface of the gripping section 41 may be formed with an unevenness or the like which serves as a slip stopper such that fingers do not easily slip when the operation wire 10 is advanced or retracted and rotated.

Figure 6:
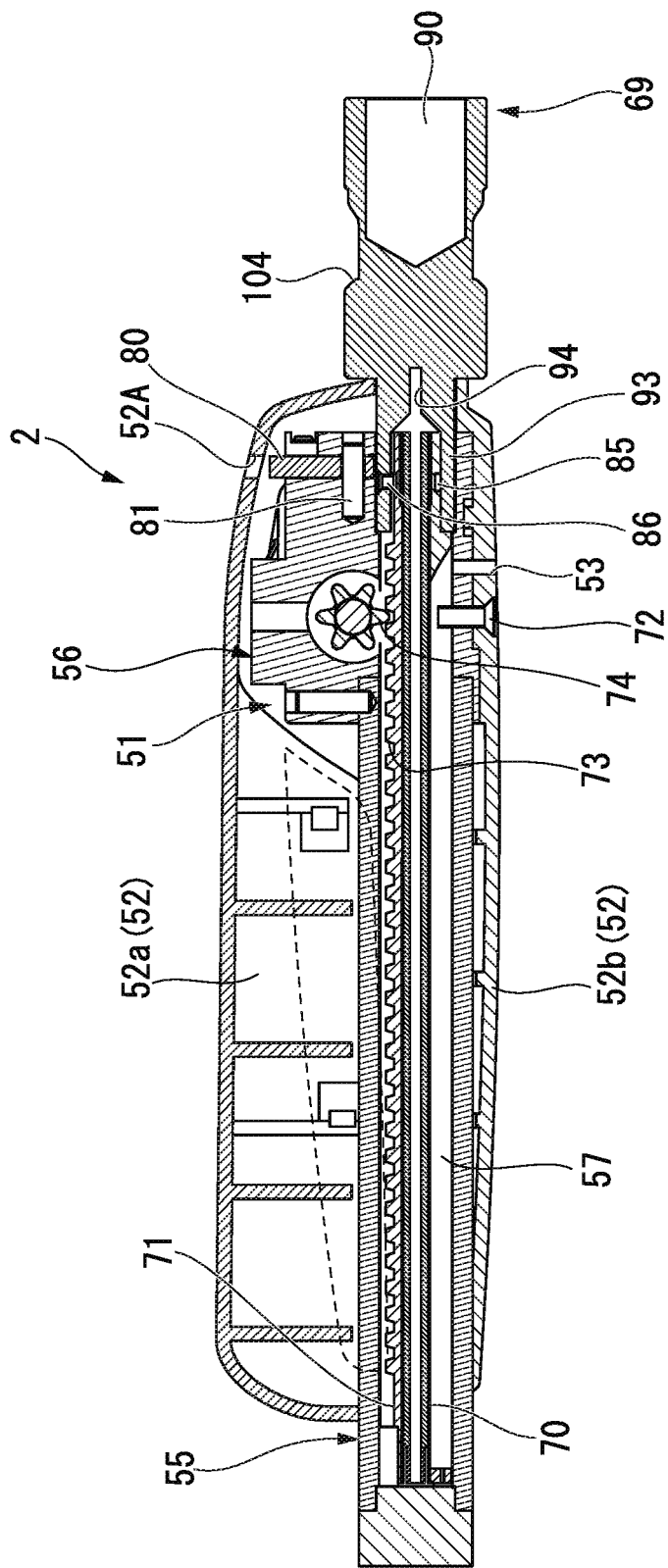
FIG. 6 is a cross-sectional view showing a stone fragmentation operation section of the stone extraction and fragmentation device.
Figure 7:
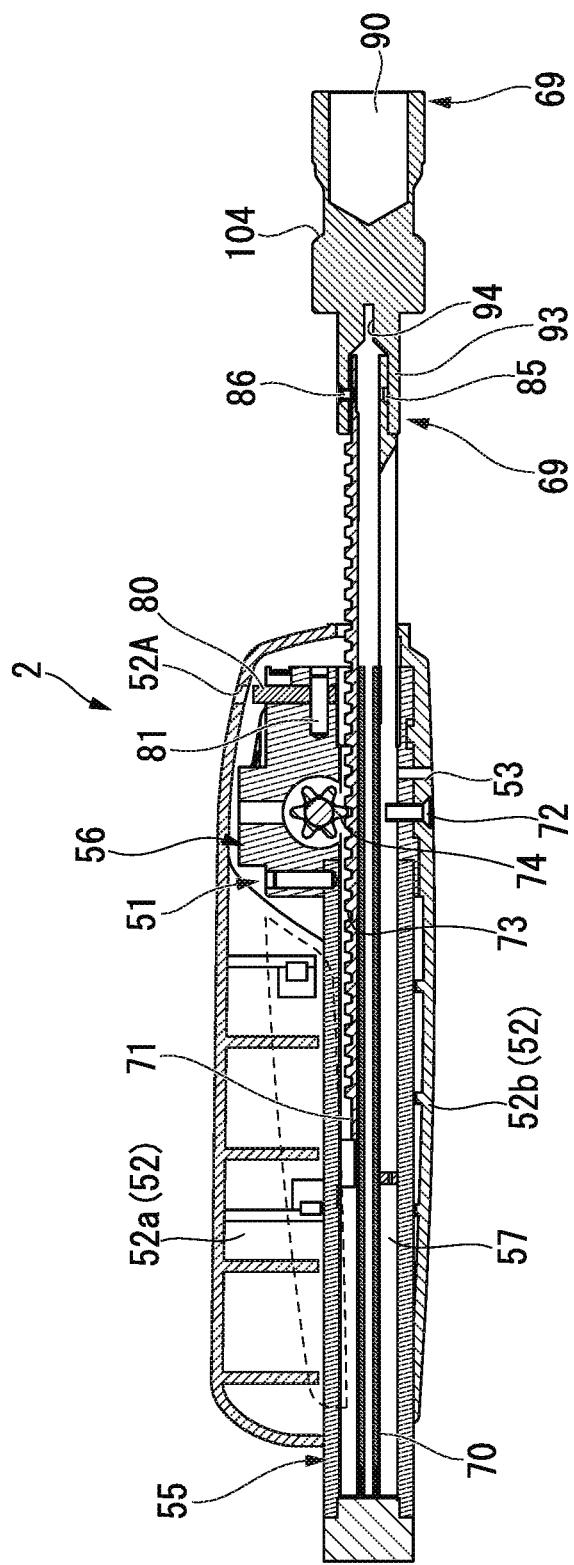
FIG. 7 is a cross-sectional view showing the stone fragmentation operation section of the stone extraction and fragmentation device.
Figure 8:
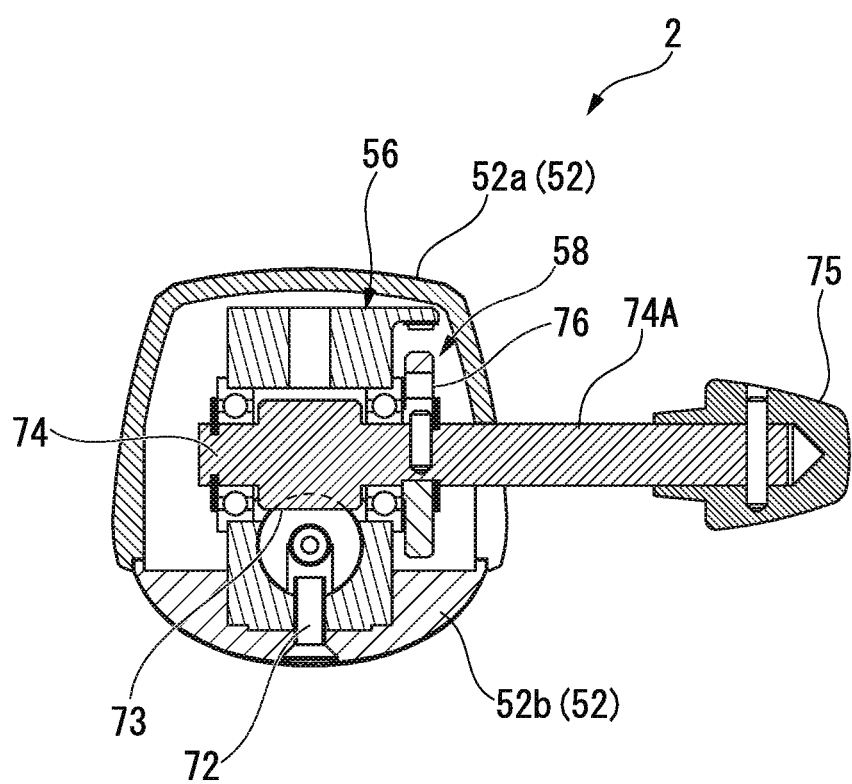
FIG. 8 is a cross-sectional view showing the stone fragmentation operation section of the stone extraction and fragmentation device.
Figure 9:
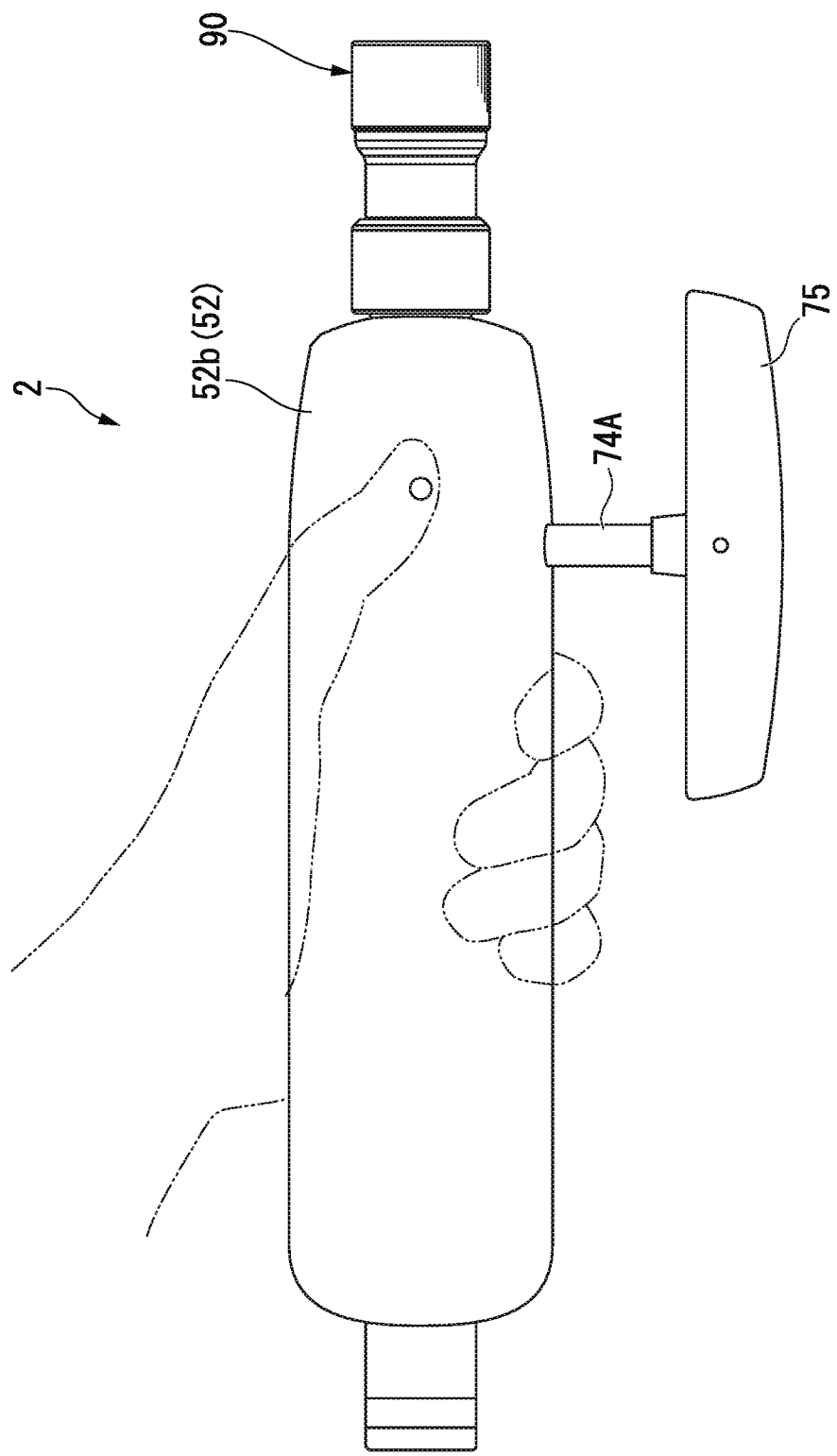
FIG. 9 is a plan view showing an outer surface of the stone fragmentation operation section of the stone extraction and fragmentation device.
Figure 10:
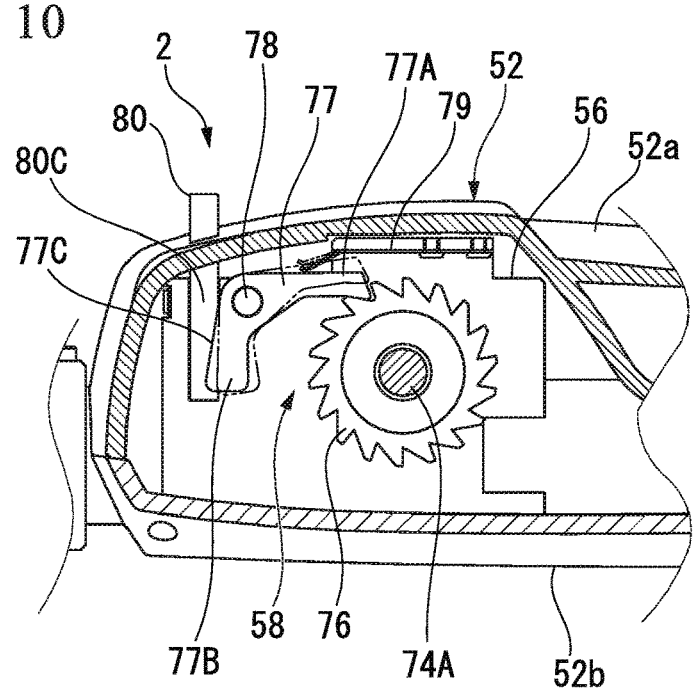
FIG. 10 is a cross-sectional view showing a ratchet mechanism of the stone extraction and fragmentation device.
Figure 11:
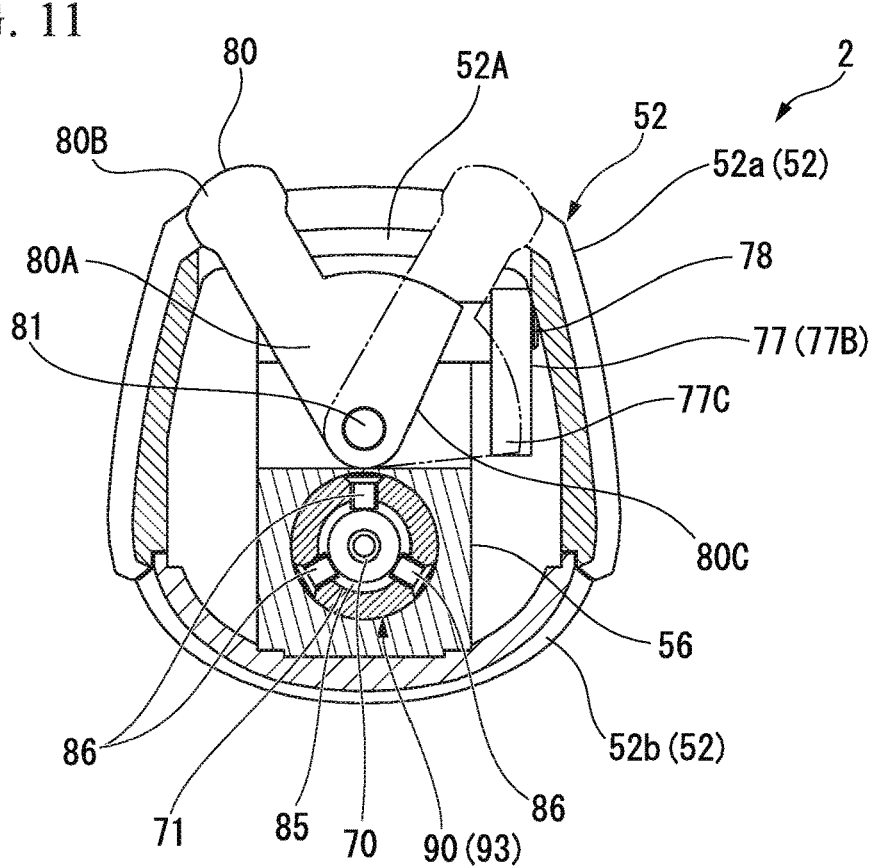
FIG. 11 is a cross-sectional view showing the ratchet mechanism of the stone extraction and fragmentation device.

Next, the stone fragmentation operation section 50 which is mounted on such a fragmenting tool 2 will be described. FIGS. 6 to 8 are cross-sectional views showing the stone fragmentation operation section 50 of the stone extraction and fragmentation device 1. FIG. 9 is a plan view showing an outer surface of the stone fragmentation operation section 50 of the stone extraction and fragmentation device 1. FIG. 10 is a cross-sectional view showing a ratchet mechanism 58 of the stone extraction and fragmentation device 1. FIG. 11 is a cross-sectional view showing the ratchet mechanism 58 of the stone extraction and fragmentation device 1, and shows a cross section which is different from that of FIG. 10.

As shown in FIG. 6, the stone fragmentation operation section 50 has a second main body 52 which is configured to be gripped by the operator, a moving body 69 which is disposed inside the second main body 52 and to which the stone extraction operation section 4 of the fragmenting tool 2 is attached, and a mechanism section 51 which is configured to advance or retreat the moving body 69.

The second main body 52 has a cover 52a and the cover 52b both of which covers the mechanism section 51 to vertically surround the mechanism section 51. The cover 52b is formed with a concave section 53 into which the pin 41b (refer to FIG. 5) formed on the gripping section 41 of the stone extraction operation section 4 of the fragmenting tool 2 is inserted. The concave section 53 restricts movement of the pin 41b in a direction which intersects an inserting or removing direction of the pin 41b. For this reason, the gripping section 41 is moved with respect to the first main body 30 in a moving direction of the moving body 69 by movement of the moving body 69 with respect to the second main body 52 in a state in which the pin 41b is inserted into the concave section 53 and the first main body 30 is attached to the moving body 69.

The moving body 69 has a rack body 71 and the joint 90.

The rack body 71 is supported at an inner circumferential side of a guide section 55 and a driving section 56, both of which will be described below, to be freely advanced or retreated. A screw 72 which is threadedly engaged from the cover 52b side prevents the rack body 71 from rotating around an axis of the rack body 71 as a rotational center. In addition, a rack 73 of a predetermined length in the axial direction is formed on the rack body 71. A pinion 74 which is meshed with the rack 73 is rotatably supported by a bearing which is fixed to the driving section 56.

The joint 90 has a bottomed cylindrical shape in which a recession, into which an engagement protrusion 30A of the first main body 30 is inserted, is formed. Also, the joint 90 has an abutting surface 94 which can come into contact with the covers 52a and 52b.

The mechanism section 51 has the cylindrical guide section 55 and the driving section 56 which is fixed to an end section of the guide section 55 by screw.

The guide section 55 and the driving section 56 are formed with through holes into which the moving body 69 is inserted. The through hole of the guide section 55 and the through hole of the driving section 56 are formed coaxially with each other. The through hole of the guide section 55 and the through hole of the driving section 56 serve as a guide hole 57 which guides the advancing or retreating of the moving body 69.

As shown in FIGS. 6 and 8, the driving section 56 has the pinion 74 which moves the rack 73, a rotating knob 75 which is fixed to a shaft 74A of the pinion 74, and the ratchet mechanism 58 which restricts rotation of the shaft 74A of the pinion 74. The shaft 74A of the pinion 74 extends outside of the cover 52a.

As shown in FIGS. 8 and 9, the rotating knob 75 is fixed to a first end that is one of both ends of the shaft 74A. The rotating knob 75 has a flat shape. A shape of the rotating knob 75 is a shape by which a surgeon can easily grasp the rotating knob 75 and the surgeon can easily apply a force to the rotating knob 75.

As shown in FIG. 8, the ratchet mechanism 58 has a gear 76 which is fixed to a second end that is the other end of both ends of the shaft 74A, a pawl 77 which is configured to be engaged with the gear 76, a support shaft 78 which joins the pawl 77 to the driving section 56, and a leaf spring 79 which biases the pawl 77 such that the pawl 77 is engaged with the gear 76.

The pawl 77 is a substantially L-shaped member which is rotatably supported by the driving section 56 via the support shaft 78, and an arm 77A which extends to a portion which is closer to the distal end side than the support shaft 78 is biased by the leaf spring 79 to be engaged with the gear 76.

The leaf spring 79 is an elastic member which is fixed to the driving section 56.

The ratchet mechanism 58 can serve to prevent rotation of the gear 76 (the pinion 74) in a direction in which the rack body 71 is moved to a distal end section. In addition, the ratchet mechanism 58 can serve to rotate the gear 76 (the pinion 74) in a stepwise manner in a direction in which the rack body 71 is pulled back in the proximal direction. The ratchet mechanism 58 can restrict the rotation of the gear 76, that is, the rotation of the pinion 74.

Another arm 77B of the pawl 77 extends downward from the support shaft 78 and toward the proximal end side, and a proximal end surface 77C is inclined to face downward and toward the proximal end. In addition, a selector switch 80 which can be engaged with the proximal end surface 77C is disposed at a portion which is closer to the proximal end side than the support shaft 78 when viewed in a side view.

As shown in FIGS. 10 and 11, the selector switch 80 has a proximal section 80B which is rotatably supported by the driving section 56 via a support shaft 81 which is parallel to the axial direction. A distal end section 80A of the selector switch 80 extends outside of the covers 52a and 52b through a slit 52A which is formed in an upper portion of the covers 52a and 52b. The proximal section 80B has a shape of a circular sector which extends to have a predetermined angle in a pivoting direction. A first lateral surface 80C of the proximal section 80B in the pivoting direction is perpendicular to the pivoting direction. Therefore, the selector switch 80 can press the proximal end surface 77C of the pawl 77. In addition, the pawl 77 is pivoted around the support shaft 78 and the engaging of the pawl 77 and the gear 76 is released when the selector switch 80 presses the proximal end surface 77C of the pawl 77 (a position of the selector switch 80 in this case is an OFF position).

When the selector switch 80 is at a position at which there is no interference against the pawl 77, the pawl 77 engages with the gear 76 and provides a ratchet function (a position of the selector switch 80 in this case is set to be an ON position).

An outer circumferential section of the proximal end side of the rack body 71 is formed with an annular groove 85, and three pins 86 are slidably inserted in the groove 85. The pins 86 are fixed to the joint 90.

Figure 12:
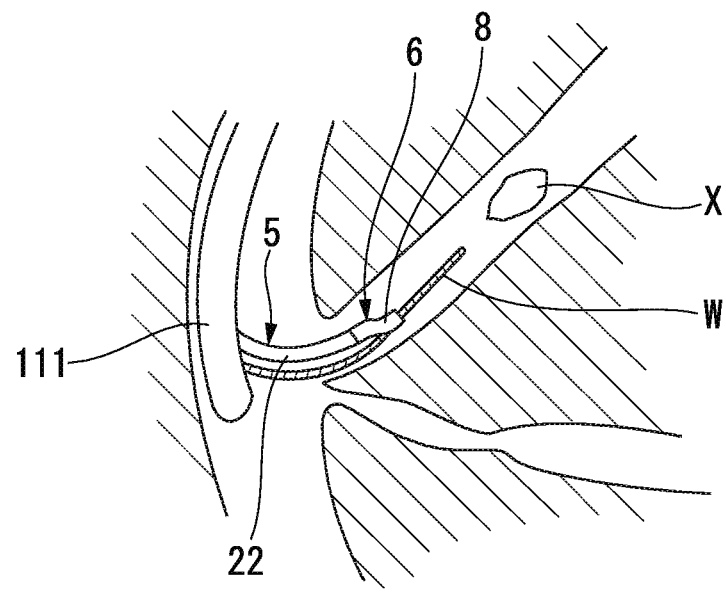
FIG. 12 is a view for describing one process when the stone extraction and fragmentation device is used.
Figure 13:
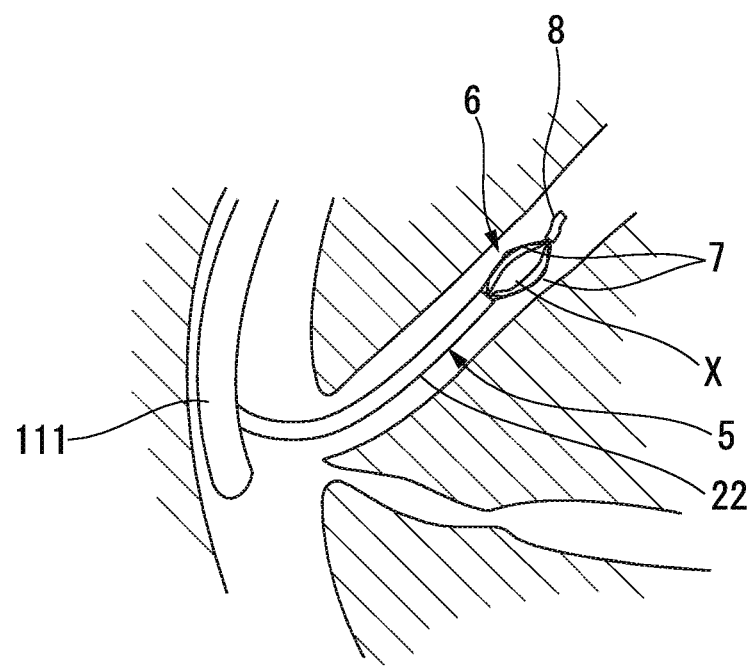
FIG. 13 is a view for describing one process when the stone extraction and fragmentation device is used.
Figure 14:
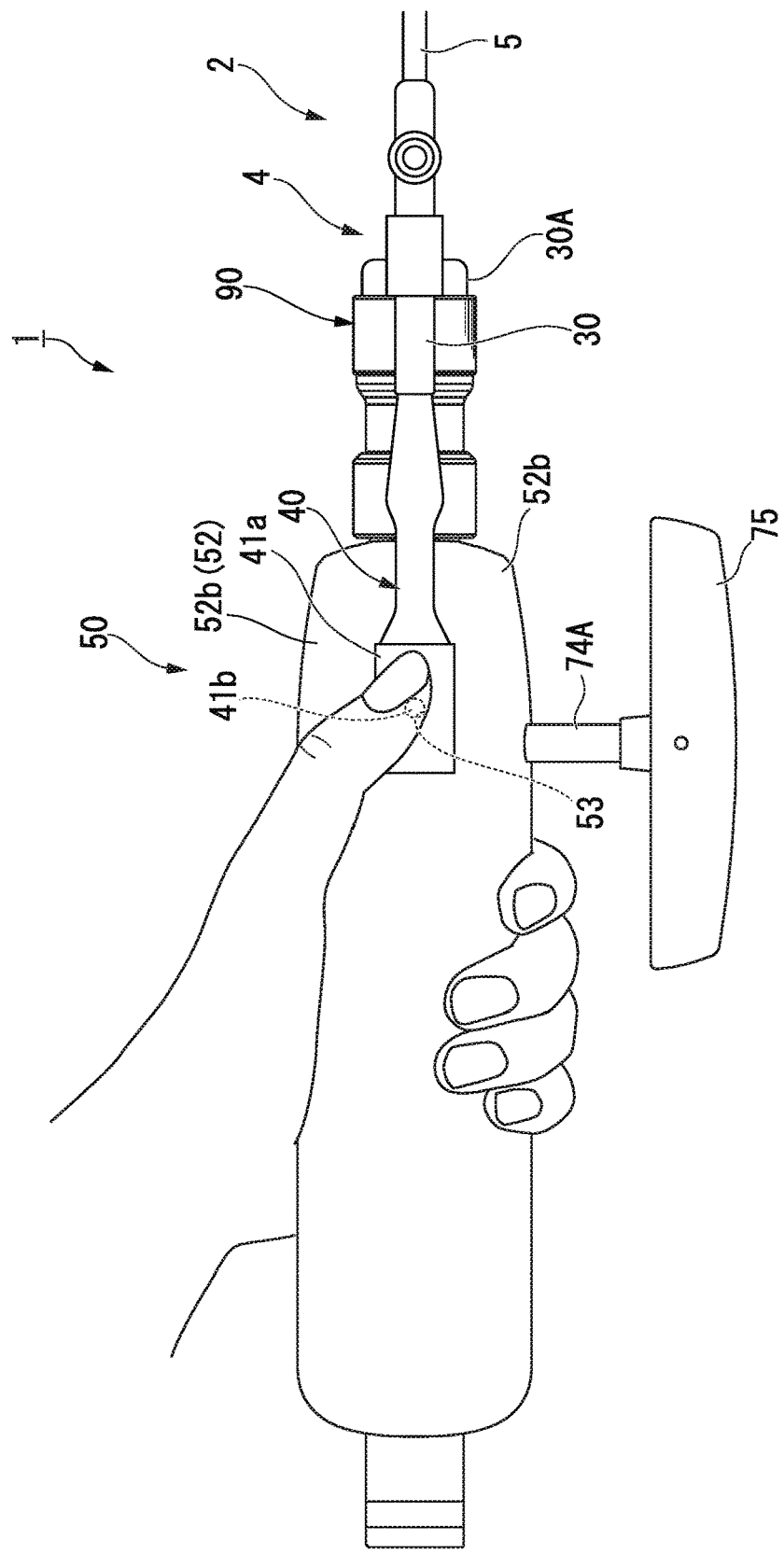
FIG. 14 is a view for describing an action of the stone extraction and fragmentation device.
Figure 15:
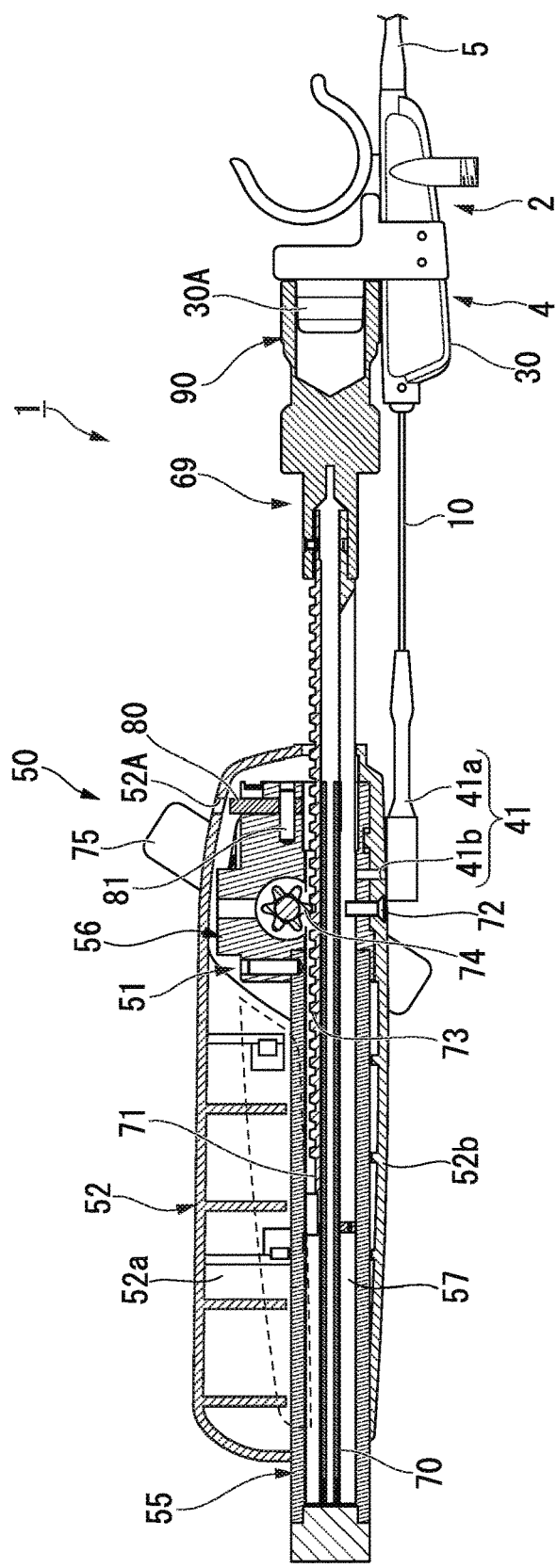
FIG. 15 is a view for describing an action of the stone extraction and fragmentation device.
Figure 16:
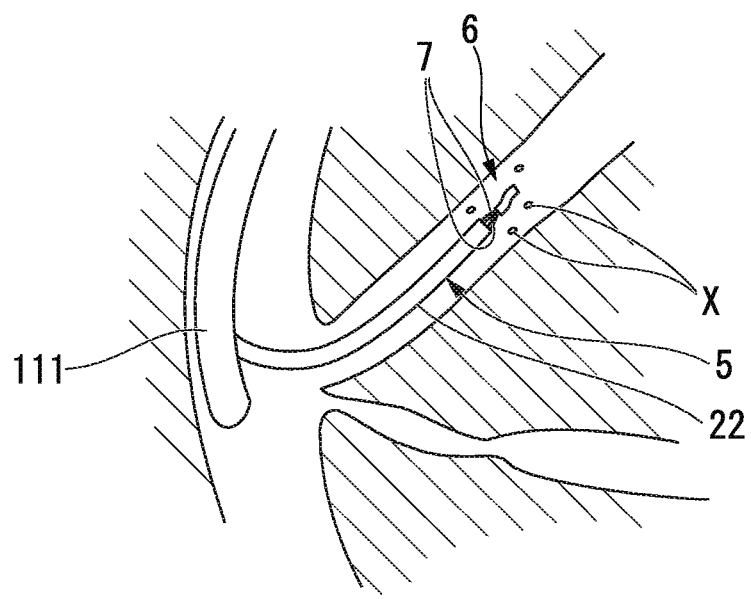
FIG. 16 is a view for describing one process when the stone extraction and fragmentation device is used.

Next, an action of the stone extraction and fragmentation device 1 of this embodiment will be described. FIGS. 12 and 13 are views for describing one process when the stone extraction and fragmentation device 1 is used. FIGS. 14 and 15 are views for describing an action of the stone extraction and fragmentation device 1. FIG. 16 is a view for describing one process when the stone extraction and fragmentation device 1 is used.

In this embodiment, when a stone does not need to be fragmented, the fragmenting tool 2 can be independently used without mounting the stone fragmentation operation section 50 to the fragmenting tool 2. As shown in FIG. 12, the fragmenting tool 2 is guided along a guide wire W using an endoscope 111 up to a lumen in which there is a stone X which is subjected to be a target on the stone extraction.

An operation of the operation wire 10 by which the basket section 6 is driven to be opened or closed is performed while the operator grips the gripping section 41 (refer to FIG. 1) which is fixed to a proximal end of the operation wire 10. This is because the operation wire 10 does not need to be moved with a strong force in a process in which stone extraction is performed by introducing the stone X into the basket section 6 as shown in FIGS. 12 and 13. In this embodiment, the stone extraction operation section 4 is more compact and lightweight than those of the stone fragmentation operation section 50, and thus is easily operated.

Next, when the stone X needs to be fragmented, an amount of force which is sufficient to fragment the stone X is not acquired only by the operator gripping the gripping section 41 and pulling the operation wire 10 in some cases. In this case, as shown in FIG. 14, the joint 90 of the stone fragmentation operation section 50 is attached to the stone extraction operation section 4, and the pin 41b of the gripping section 41 is inserted into the concave section 53 of the cover 52b of the second main body 52 of the stone fragmentation operation section 50. Subsequently, when the rotating knob 75 is rotated, as shown in FIG. 15, the pinion 74 is rotated to move the rack body 71. The pinion 74 moves the rack body 71 so that the moving body 69 causes the stone extraction operation section 4 and the gripping section 41 being away from each other. An operation of the moving body 69 which spaces apart the stone extraction operation section 4 and the gripping section 41 is an operation which retracts the basket section 6 into the insertion section 5 by pulling the operation wire 10 in the stone extraction operation section 4.

The rotating knob 75 is used so that the operation wire 10 can be pulled by a force which is greater than that when the gripping section 41 is gripped and the operation wire 10 is pulled. As a result, as shown in FIG. 16, the stone is fragmented by driving of the basket section 6 with sufficient amount of force to fragment the stone.

As described above, in this embodiment, the stone extraction and fragmentation device 1 is easily operated in the treatment of extracting stone in which the stone does not need to be fragmented because stone extraction and fragmentation device 1 is compact and lightweight, and a sufficient amount of force can be applied with a light force when the stone needs to be fragmented. As a result, in this embodiment, the stone extraction and fragmentation device 1 which easily performs an operation is provided to both extract and fragment the stone.

Second Embodiment

Figure 17:
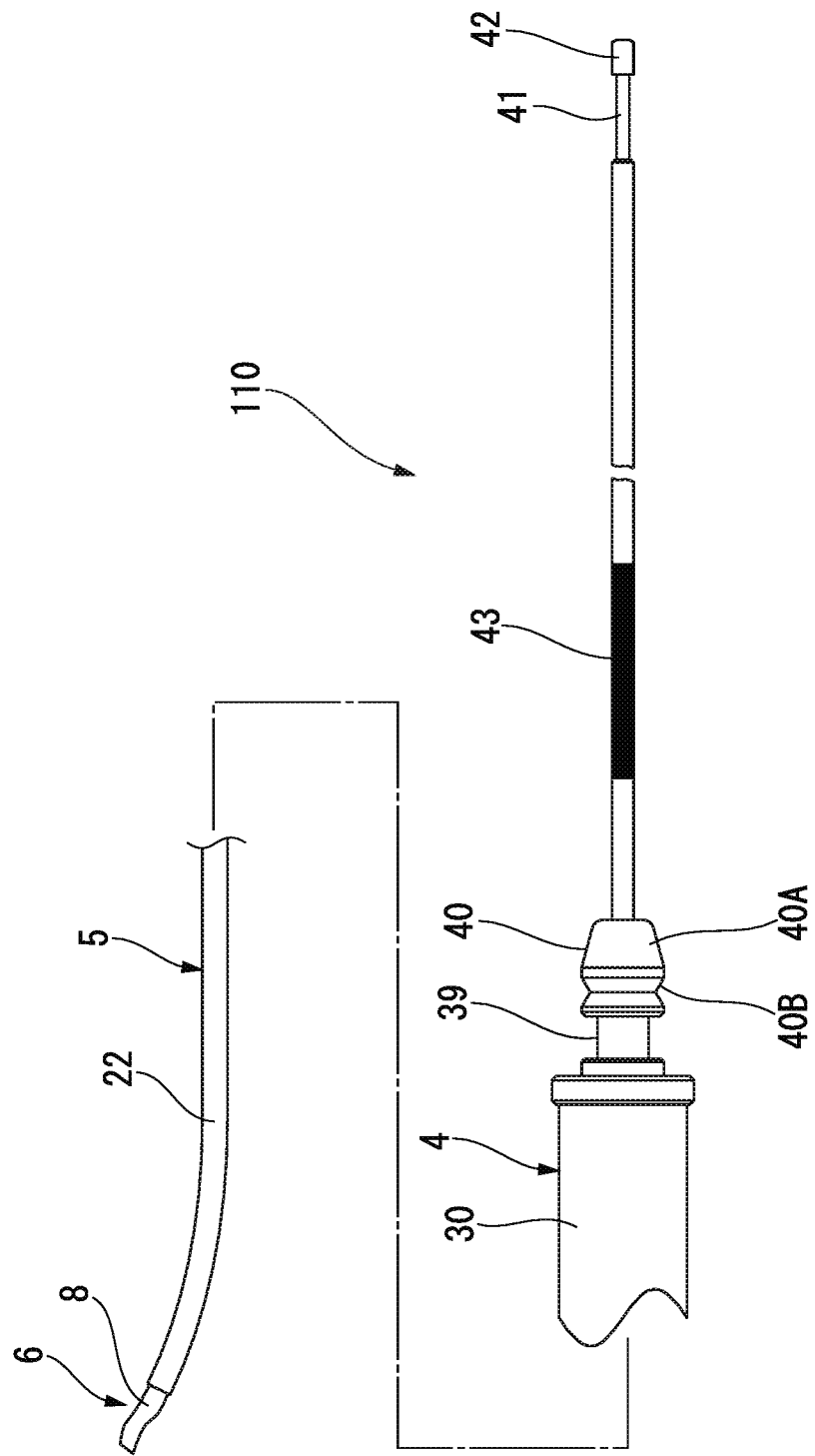
FIG. 17 is a side view showing a fragmenting tool of a stone extraction and fragmentation device of a second embodiment of the present invention.
Figure 18:
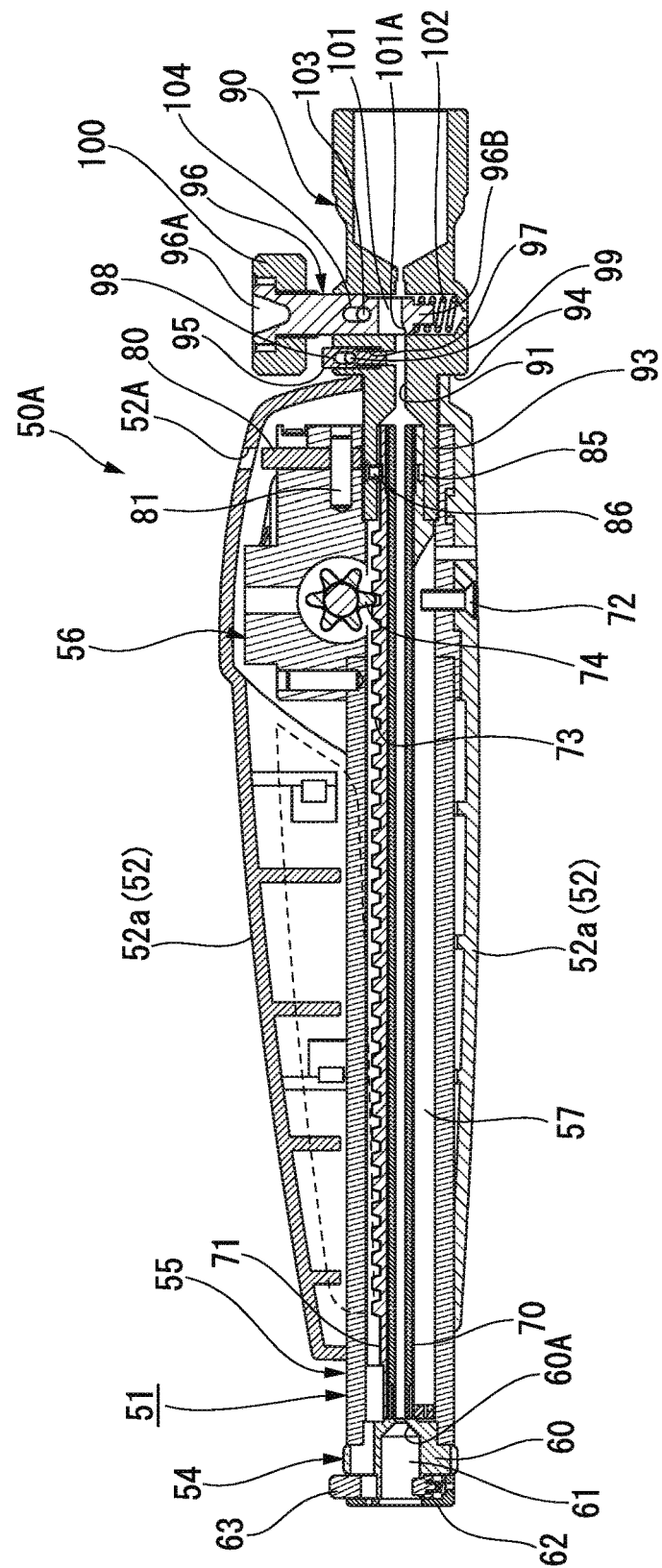
FIG. 18 is a cross-sectional view showing a stone fragmentation operation section of a stone extraction and fragmentation device of the embodiment.
Figure 19:
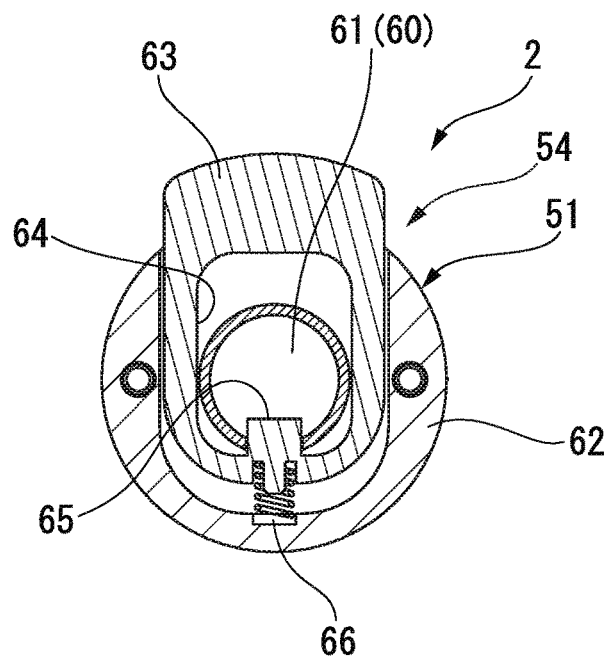
FIG. 19 is a cross-sectional view showing an end connecting section of the stone fragmentation operation section.
Figure 20:
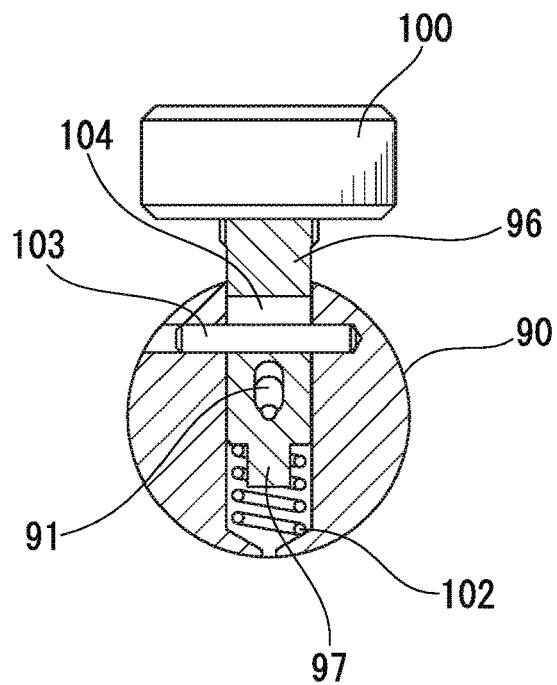
FIG. 20 is a cross-sectional view showing a joint of the stone fragmentation operation section.
Figure 21:
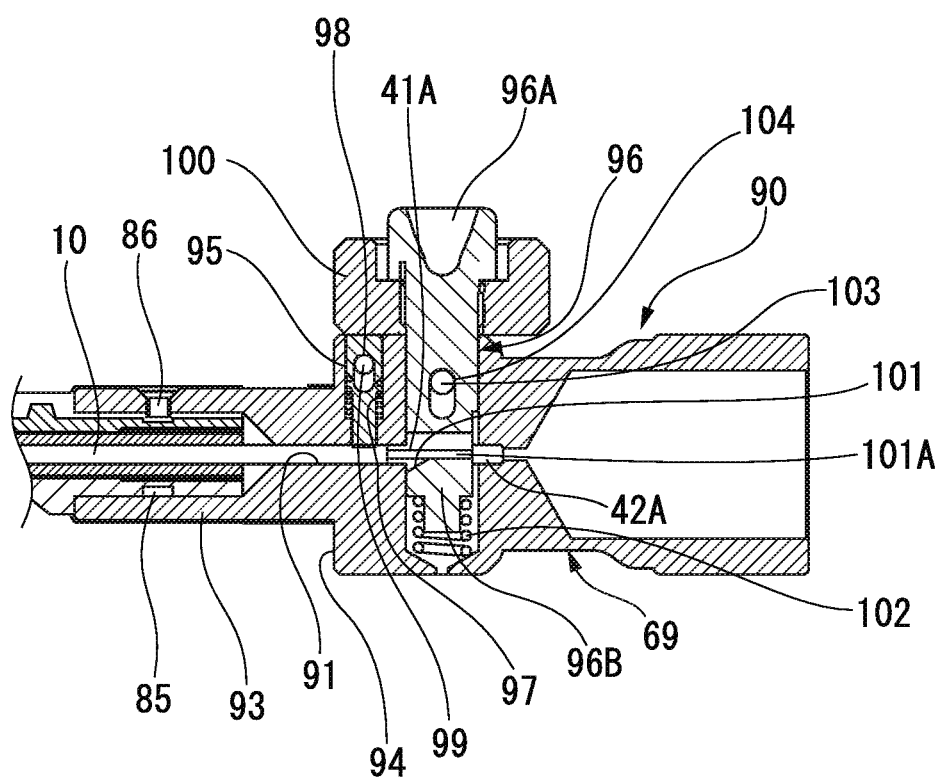
FIG. 21 is a cross-sectional view showing a joint of the stone fragmentation operation section.
Figure 22:
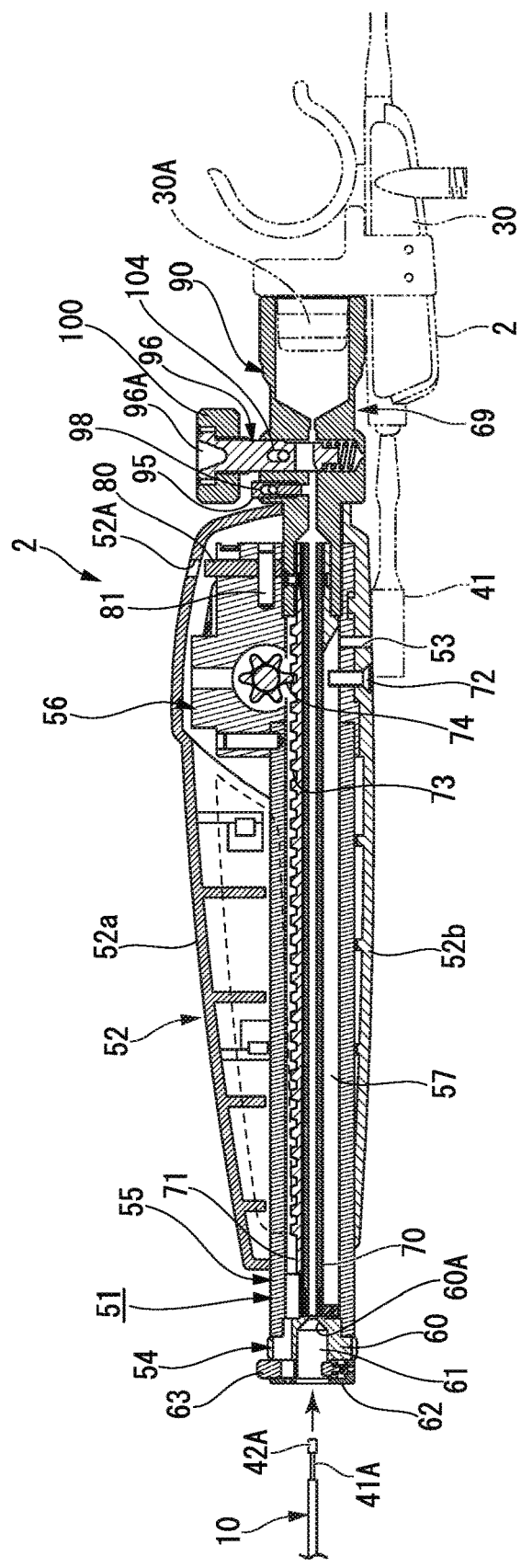
FIG. 22 is a cross-sectional view for describing an action of the stone fragmentation operation section.

A second embodiment of the present invention will be described. In this embodiment, the same components as those which were previously described in the first embodiment are denoted with the same reference numerals as those of the first embodiment, and overlapping descriptions thereof will be omitted. FIG. 17 is a side view showing a fragmenting tool 110 of a stone extraction and fragmentation device 1A of this embodiment. FIG. 18 is a cross-sectional view showing a stone fragmentation operation section 50A of the stone extraction and fragmentation device 1A. FIG. 19 is a cross-sectional view showing an end connecting section 54 of the stone fragmentation operation section 50A. FIG. 20 is a cross-sectional view showing a joint 90 of the stone fragmentation operation section 50A. FIG. 21 is a cross-sectional view showing the joint 90 of the stone fragmentation operation section 50A. FIG. 22 is a cross-sectional view for describing an action of the stone fragmentation operation section 50A.

A constitution of this embodiment is different from that of the above-described first embodiment in that the stone fragmentation operation section 50A (refer to FIG. 18) to which the well-known fragmenting tool 110 (refer to FIG. 17) having a structure that is partially different from that of the above-described fragmenting tool 2 can be attached is provided in addition to the fragmenting tool 2 which is described in the first embodiment.

A constitution of the fragmenting tool 110 in this embodiment will be described.

As shown in FIG. 17, the fragmenting tool 110 has a reduced diameter section 41A in which a portion of a proximal end portion of an operation wire 10 is reduced in diameter and a falling-out retaining tip 42A which is fixed to a proximal end of the reduced diameter section 41A instead of the gripping section 41 which is described in the above-described first embodiment.

In addition, the fragmenting tool 110 has an engagement section 40 by which a first main body 30 is joined to the stone fragmentation operation section 50A at a proximal end of the first main body 30. The engagement section 40 of the fragmenting tool 110 has a tapered surface 40A which is configured to guide to be inserted into the stone fragmentation operation section 50A and a tapered surface 40B which serves as a falling-out retainer from the stone fragmentation operation section 50A.

The fragmenting tool 110 has the same constitution as the fragmenting tool 2 in the first embodiment excluding a constitution near the stone extraction operation section 4 which is different from the fragmenting tool 2.

The fragmenting tool 110 of this embodiment is an instrument in which the operator may move the operation wire 10 while gripping the reduced diameter section 41A or the falling-out retaining tip 42A, but the reduced diameter section 41A or the falling-out retaining tip 42A is intended to be appropriately joined to the stone fragmentation operation section 50A.

In the stone fragmentation operation section 50A of this embodiment, as shown in FIG. 18, a mechanism section 51 further has the end connecting section 54 configured to attach the fragmenting tool 110.

As shown in FIGS. 18 and 19, the end connecting section 54 has a ring body 60. A tapered surface 60A, which can receive the engagement section 40 formed on a cap 39 at the fragmenting tool 2 side, is formed at an inner hole 61 of the ring body 60.

A proximal end of the ring body 60 is opened to be able to insert only the operation wire 10. A cap 62 is fixed to a portion which is closer to a distal end side than the ring body 60 by screws. The cap 62 is formed with a hole which is substantially the same as the inner hole 61. In addition, a sheath connecting button 63 is movably inserted into a gap between the cap 62 and the ring body 60 in a direction which is perpendicular to an axis.

The sheath connecting button 63 has an elongated hole 64 which extends in a moving direction thereof. A long axis of the elongated hole 64 is longer than a maximum diameter of the inner hole 61 of the ring body 60, and a short axis of the elongated hole 64 is substantially the same as the maximum diameter of the inner hole 61 of the ring body 60. An engaging protrusion 65 projects from a lower end of the elongated hole 64 to reduce an opening area of the elongated hole 64, and an opening of the sheath connecting button 63 is formed in a U shape as a whole. The sheath connecting button 63 is biased with respect to the ring body 60 by an elastic member 66 such as a coil spring. The sheath connecting button 63 is at a position at which the engaging protrusion 65 projects and an opening area of the inner hole 61 of the ring body 60 is thus reduced in its natural state. Note that, when the sheath connecting button 63 is pushed, the engaging protrusion 65 retreats, and the opening area of the inner hole 61 can thus be secured.

A guide tube 70 is fixed to the proximal end of the ring body 60 of the end connecting section 54 to be in communication with the inner hole 61. The guide tube 70 extends inside a guide hole 57 of the mechanism section 51 coaxially with the mechanism section 51. The rack body 71 is mounted on the guide tube 70 in an axial direction to be freely advanced or retreated to cover an outer circumference thereof.

Also, in this embodiment, as shown in FIG. 21, the moving body 69 can fix the operation wire 10 to the moving body 69 using the reduced diameter section 41A and the falling-out retaining tip 42A both of which are formed at the operation wire 10 of the fragmenting tool 110. In other words, the joint 90 has a hole 91 into which the proximal end portion of the operation wire 10 is inserted and a wire connecting button 96 which is capable of being engaged with the reduced diameter section 41A of the operation wire 10 inserted into the hole 91.

As shown in FIGS. 18 and 20, in the wire connecting button 96, a stopper 100 is threadedly engaged with a head 96A which projects from the joint 90, and a distal end section 96B of the wire connecting button 96 is retracted into the joint 90, extends over the hole 91, and is biased with respect to the joint 90 by an elastic member 102 such as a coil spring. A biasing direction of the elastic member 102 is a direction in which the wire connecting button 96 is pushed out of the joint 90, and falling-out of the elastic member 102 from the joint 90 is prevented by passing a retaining pin 103 with respect to an elongated hole 104 of the wire connecting button 96.

Also, as shown in FIG. 18, an insertion hole 101 is formed between the head 96A and the distal end section 96B of the wire connecting button 96. The insertion hole 101 passes through the wire connecting button 96 in parallel with an axis of the joint 90. When the wire connecting button 96 is pushed, the insertion hole 101 is formed at a position at which a center of the insertion hole 101 and a center of the hole 91 of the joint 90 substantially coincide with each other, and an inner circumference of a distal end side of the insertion hole 101 is formed with a tapered surface 101A to be open toward the distal end thereof. When the wire connecting button 96 is biased by the elastic member 102 in its natural state, the tapered surface 101A is disposed on an axis of the hole 91 of the joint 90.

The stopper 100 is a member having an annular shape which is enlarged rather than the outer circumference of the head 96A of the wire connecting button 96. When the stopper 100 is screwed toward the joint 90, a stroke of the wire connecting button 96 in a direction in which the wire connecting button 96 is pushed to the joint 90 can be accordingly restricted. In addition, the stopper 100 moves a pin 95 inserted into an insertion hole 97 which is in communication with the hole 91 along the insertion hole 97.

Since an outer diameter of the stopper 100 is longer than a distance between an axis of the wire connecting button 96 and an axis of the pin 95, the stopper 100 presses an head of the pin 95 while the stopper 100 is screwed so that the pin 95 is pushed toward the hole 91.

Next, an action of this embodiment will be described.

First, when the fragmenting tool 110 is mounted on the stone fragmentation operation section 50A, after the operation wire 10 is pulled until a marking 43 of a proximal end side of the operation wire 10 is exposed as shown in FIG. 17, the proximal end of the operation wire 10 is inserted into the guide tube 70 from the end connecting section 54 of the stone fragmentation operation section 50A as shown in FIG. 22. When the operation wire 10 is settled inside the stone fragmentation operation section 50A, the cap 39 of the fragmenting tool 110 enters the inner hole 61 of the end connecting section 54. At this time, the stone extraction operation section 4 of the fragmenting tool 110 is mounted on the stone fragmentation operation section 50A only by inserting the cap 39 into the end connecting section 54. To be specific, since the tapered surface 40A of the engagement section 40 of the cap 39 comes into contact with a protrusion 65 of the sheath connecting button 63, the protrusion 65 is pressed in a direction in which the elastic member 66 is compressed by pushing of the cap 39. As a result, since the entire sheath connecting button 63 is moved to widen an opening area, when the cap 39 is directly pushed, an abutting surface 39A of the cap 39 comes into contact with the cap 62 of the ring body 60. At this time, a position of the cap 39 coincides with a protruding position of the protrusion 65, the sheath connecting button 63 is returned by a restoring force of the elastic member 66, and the protrusion 65 is thus engaged with a concave section in the cap 39. For example, a convex section which is provided at the cap 62 is meshed with a concave section which is provided in the abutting surface 39A when the fragmenting tool 110 is mounted and the fragmenting tool 110 cannot be rotated such that a proximal end of the fragmenting tool 110 which is attached is not freely rotated with respect to the stone fragmentation operation section 50A in a circumferential direction.

As shown in FIG. 21, the falling-out retaining tip 42A of the operation wire 10 enters the joint 90 and comes into contact with the tapered surface 101A of the wire connecting button 96 which is on a passage of the hole 91. When the operation wire 10 is further inserted, the tapered surface 101A is pushed so that the entire wire connecting button 96 is moved in a direction in which the elastic member 102 is compressed. As a result, a communication area of the insertion hole 101 and the hole 91 is increased, and the operation wire 10 is inserted up to a proximal end of the joint 90 over the wire connecting button 96.

At this time, a position in which the reduced diameter section 41A of the operation wire 10 is formed coincides with a position of the insertion hole 101 of the wire connecting button 96, the wire connecting button 96 is returned by a restoring force of the elastic member 102, and the wire connecting button 96 and the joint 90 are in cooperation with each other to pinch the operation wire 10. Thus, movement of the operation wire 10 in an axial direction is prevented. Note that, when the joint 90 is pulled out of the mechanism section 51 as an initial state, the end connecting section 54 and the cap 39 are initially connected, and the operation wire 10 is connected when the joint 90 is pushed. A mechanism at the time of connection is the same as described above.

Here, since the operation wire 10 idles with respect to the joint 90 in this state, as shown in FIG. 21, the stopper 100 is screwed so that the pin 95 is pushed. The operation wire 10 is pinched by the pin 95 and an inner circumferential surface of the hole 91, and the joint 90 and the operation wire 10 can be integrally rotated.

When the pin 95 is not provided, the operation wire 10 can be fixed to be able to be integrally rotated by only the wire connecting button 96, but a fixing force when the pin 95 is provided is greater than that when the pin 95 is not provided. Also, since the stopper 100 comes into contact with the pin 95, even if the wire connecting button 96 is attempted to be pushed, the wire connecting button 96 is not moved, and the connection of the operation wire 10 and the joint 90 is not released in use.

A procedure in which the stone extraction and fragmentation device 1A is used is substantially the same as the above-described first embodiment, and stone extraction and fragmenting stone can be performed using the stone fragmentation operation section 50A. In addition, in this embodiment, as shown in FIG. 22, the stone fragmentation operation section 50A can appropriately attach both of the fragmenting tool 2 which is described in the first embodiment and the fragmenting tool 110 in this embodiment.

The embodiments of the present invention have been described in detail above with reference to the drawings, but specific configurations are not limited to the embodiments and design modifications or the like can also be made within the scope of the present invention without departing from the gist of the present invention.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A stone extraction and fragmentation device comprising:
    a fragmentation tool; and
    a handle,
    the fragmentation tool comprising:
        a tubular section configured to be inserted into a channel of an endoscope;
        a treatment section located at a distal end of the tubular section;
        a first main body connected to a proximal end of the tubular section;
        an operation wire inserted in the tubular section to be able to be advanced or retracted, the operation wire being connected to the treatment section, a proximal end portion of the operation wire being configured to protrude proximally from the first main body; and
        a gripping section fixed to a proximal-most end of the operation wire, the gripping section being configured to be advanced or retracted with respect to the first main body;
    the handle comprising:
        a second main body connected to the gripping section;
        a moving body provided at the second main body, the moving body having a longitudinal axis and the moving body being configured to advance and retract along the longitudinal axis with respect to the second main body;
        a rotation shaft having an end part configured to protrude from an outer periphery of the second main body, the rotation shaft being configured to be rotatable around a longitudinal axis of the rotation shaft; and a rotating knob fixed to the end part of the rotation shaft, the rotating knob, when rotated, being configured to advance or retract the moving body with respect to the second main body, wherein the moving body is configured to move the first main body in a direction away from the second main body by rotation of the rotating knob, the gripping section has one of a protrusion or a cavity that engages with the other of the protrusion or the cavity disposed on the outer periphery of the second main body;

the longitudinal axis of the rotation shaft intersects with the longitudinal axis of the moving body; and engagement between the protrusion and the cavity is configured to be detached along an axis direction intersecting with the longitudinal axis of the rotation shaft and the longitudinal axis of the moving body.

2. The stone extraction and fragmentation device according to claim 1, wherein the operation wire and the moving body are configured to be advanced and retracted along different axes from each other.

3. The stone extraction and fragmentation device according to claim 1, further comprising:
a first operation section which is provided at the proximal end of the tubular section; and
a second operation section which is capable of being attached to and detached from the first operation section, wherein
the first operation section has the first main body and the gripping section, and
the second operation section has the second main body, the moving body, and the rotating knob.

4. The stone extraction and fragmentation device according to claim 3, wherein the second operation section is configured to operate the gripping section moving in a direction away from the first main body in accordance with moving the moving body in a direction away from the second operation section using rotation of the rotating knob.

5. The stone extraction and fragmentation device according to claim 1, wherein:
the moving body includes a rack that extends in the direction along a longitudinal axis of the operation wire; and
a joint formed in a distal end of the rack, the joint being configured to be detachable from the first main body.

6. The stone extraction and fragmentation device according to claim 5, wherein:
the second main body includes a pinion that is meshed with the rack, and
the rotating knob is configured to rotate around a rotation axis of the pinion.

7. The stone extraction and fragmentation device according to claim 6, wherein:
the first main body includes an engagement protrusion that is substantially cylindrical-shaped,
the moving body includes a joint that has a recession in which the engagement protrusion is inserted,
the gripping section includes the protrusion, and
the second main body includes the cavity in which the protrusion is inserted.

8. The stone extraction and fragmentation device according to claim 1, wherein:
the first main body includes an engagement protrusion that is substantially cylindrical-shaped,
the moving body includes a joint that has a recession in which the engagement protrusion is inserted,
the gripping section includes the protrusion, and
the second main body includes the cavity in which the protrusion is inserted.

9. The stone extraction and fragmentation device according to claim 1, further comprising another fragmentation tool that includes a second operation wire, wherein
an opening into which the second operation wire is configured to be inserted is formed in a proximal end of the second main body;
the second operation wire inserted into the opening is configured to be engaged with the moving body; and
the second main body is capable of being selectively engaged with the gripping section or the second operation wire.

10. The stone extraction and fragmentation device according to claim 1, wherein the other of the protrusion or the cavity on the outer periphery of the second body is extended along the axis in a direction intersecting with the longitudinal axis of the rotation shaft and the longitudinal axis of the moving body.

11. A handle for use with a fragmentation tool, the fragmentation tool comprising: a tubular section configured to be inserted into a channel of an endoscope; a treatment section located at a distal end of the tubular section; a first main body connected to a proximal end of the tubular section; an operation wire inserted in the tubular section to be able to be advanced or retracted, the operation wire driving the treatment section, a proximal end portion of the operation wire being configured to protrude proximally from the first main body; and a gripping section fixed to a proximal-most end of the operation wire, the gripping section being configured to be advanced or retracted with respect to the first main body, the handle comprising:
a second main body configured to detachably connect the fragmentation tool;
a moving body provided at the second main body, the moving body having a longitudinal axis and the moving body being configured to advance and retract along the longitudinal axis with respect to the second main body;
a rotation shaft configured to be rotatable around a longitudinal axis of the rotation shaft; and
a rotating knob fixed to an end part of the rotation shaft, the rotating knob being configured to cause the moving body to be advanced or retracted with respect to the second main body, wherein
the second main body is configured to be connected to the gripping section,
the moving body is configured to be connected to the first main body,
the moving body is configured to move the first main body in a direction away from the second main body by rotation of the rotating knob,
the gripping section has one of a protrusion or a cavity that engages with the other of the protrusion or the cavity disposed on an outer periphery of the second main body,
the end part of the rotation shaft configured to protrude from the outer periphery of the second main body and the end part being fixed to the rotating knob;
the longitudinal axis of the rotation shaft intersects with the longitudinal axis of the moving body; and
engagement between the protrusion and the cavity is configured to be detached along an axis in a direction intersecting with the longitudinal axis of the rotation shaft and the longitudinal axis of the moving body.

12. The handle for a stone extraction and fragmentation according to claim 11, further comprising another fragmentation tool that includes a second operation wire,
wherein
an opening into which the second operation wire is configured to be inserted is formed in a proximal end of the second main body;
the second operation wire inserted into the opening is configured to be engaged with the moving body; and
the second main body is capable of being selectively engaged with the gripping section or the second operation wire.

13. The handle for use with a fragmentation tool according to claim 11, wherein the other of the protrusion or the cavity on the outer periphery of the second body is extended along the axis in a direction intersecting with the longitudinal axis of the rotation shaft and the longitudinal axis of the moving body.

14. A fragmentation tool for stone extraction, the fragmentation tool comprising:
a tubular section configured to be inserted into a channel of an insertion section of an endoscope;
a treatment section located at a distal end of the tubular section;
a first main body connected to a proximal end of the tubular section;
an operation wire inserted in the tubular section to be able to be advanced or retracted, the operation wire being connected to the treatment section, a proximal end portion of the operation wire being configured to protrude proximally from the first main body; and
a gripping section fixed to a proximal-most end of the operation wire, the gripping section being configured to be advanced or retracted with respect to the first main body and the gripping section is detachably connected to a handle;
wherein the handle comprising:
a second main body connected to the gripping section;
a moving body provided at the second main body, the moving body having a longitudinal axis and the moving body being configured to advance and retract along the longitudinal axis with respect to the second main body;
a rotation shaft having an end part protruding from an outer periphery of the second main body and the rotation shaft being configured to be rotatable around a longitudinal axis of the rotation shaft; and
a rotating knob fixed to the end part of the rotation shaft, the rotating knob being configured to cause the moving body to be advanced or retracted with respect to the second main body,
wherein the moving body is configured to be connected to the first main body,
the gripping section has one of a protrusion or a cavity that engages with the other of the protrusion or the cavity disposed on the outer periphery of the second main body;
the longitudinal axis of the rotation shaft intersects with the longitudinal axis of the moving body; and
engagement between the protrusion and the cavity is configured to be detached along an axis in a direction intersecting with the longitudinal axis of the rotation shaft and the longitudinal axis of the moving body.

15. The fragmentation tool for stone extraction according to claim 14, further comprising another fragmentation tool that includes a second operation wire,
wherein
an opening into which the second operation wire is configured to be inserted is formed in a proximal end of the second main body;
the second operation wire inserted into the opening is configured to be engaged with the moving body; and
the second main body is capable of being selectively engaged with the gripping section or the second operation wire.

16. The fragmentation tool for stone extraction according to claim 14, wherein the other of the protrusion or the cavity on the outer periphery of the second body is extended along the axis in a direction intersecting with the longitudinal axis of the rotation shaft and the longitudinal axis of the moving body.

* * * * *